United States Patent
Mannschedel et al.

(10) Patent No.: US 6,254,392 B1
(45) Date of Patent: Jul. 3, 2001

(54) MEANS FOR FILLING ROOT CANALS AND PREPARATION METHOD

(75) Inventors: Werner Mannschedel, Langenau; Rolf Herrmann, Günzburg, both of (DE)

(73) Assignee: ROEKO GmbH, Langenau (DE)

( * ) Notice: Subject to any disclaimer, the term of this patent is extended or adjusted under 35 U.S.C. 154(b) by 0 days.

(21) Appl. No.: 09/295,698

(22) Filed: Apr. 21, 1999

(30) Foreign Application Priority Data

Apr. 22, 1998 (DE) .............................. 198 17 846

(51) Int. Cl.[7] .................................................. A61C 5/02
(52) U.S. Cl. .................................................. 433/224; 433/27
(58) Field of Search .................................. 433/224, 228.1, 433/27, 81; 106/35

(56) References Cited

U.S. PATENT DOCUMENTS

| | | | |
|---|---|---|---|
| 4,525,147 | * | 6/1985 | Pitz et al. .............................. 433/224 |
| 5,741,139 | * | 4/1998 | Sicurelli, Jr. et al. ................ 433/220 |
| 5,893,713 | * | 4/1999 | Garman et al. ......................... 433/32 |

* cited by examiner

Primary Examiner—John J. Wilson
Assistant Examiner—Melba Bumgarner
(74) Attorney, Agent, or Firm—Pitney, Hardin, Kipp & Szuch, LLP

(57) ABSTRACT

The invention relates to a filling means (1) for root canals in humans and animals, having a proximal end (5) and a distal end (4), which filling means comprises an elongate electrically conductive element (2) sheathed in an isoprene-based matrix (3), characterized in the distal end of the electrically conductive element lies exposed. The invention relates also to a method of preparing the filing means according to the invention.

14 Claims, 1 Drawing Sheet

MEANS FOR FILLING ROOT CANALS AND PREPARATION METHOD

FIELD OF THE INVENTION

The present invention relates to an elongate means (1) for filling root canals in humans and animals that includes an elongate electrically conductive element (2) sheathed in an isoprene-based matrix (3), wherein in that one end of the electrically conductive element lies exposed. It relates also to a method of preparing the filling means.

BACKGROUND ART

For the treatment of the disorder known as pulpitis, the diseased pulpa is removed mechanically from the root canal, and the root canal is cleaned and drilled out, filled with an elastic-plastic element or with a different filling material and then sealed. For the prior art, see, for example, Friedman et al. In J. Dent. Res., 54 (1975) 921–925, Briseno in Philipp J., 2, 90, 65–73 and U.S. Pat. No. 4,632,977. As root canal filling materials Briseno describes inter alia semi-rigid cements based on synthetic resin, zinc oxide eugenol, calcium hydroxide or glass ionomer. U.S. Pat. No. 4,632,977 proposed trans-polyisoprene-based filling materials, for example based on gutta-percha or balata. Gutta-percha points are commercially available, the standard composition thereof being 20% by weight of gutta-percha as matrix, from 60 to 75% by weight of zinc oxide as filler, from 1 to 17% by weight of heavy metal sulphates as X-ray contrast agent and from 3 to 4% by weight of waxes and resins as softener. This filling material is inert in the root canal and accordingly does not react with body tissue.

The determination of the exact working length in a root canal is one of the most important working steps of the endodontological treatment in the treatment of pulpitis and is crucial in terms of success or failure. The preparation of a tooth should end just before the apex, namely in the apical constriction, that is to say the narrowest portion of the root canal. If the root canals are not prepared to a sufficient depth and if the gutta-percha points used to seal the root canal are not pushed far enough into the root canal, bacteria may multiply in the remainder of the root canal, which will cause the patient problems. If the gutta-percha points are pushed beyond the root canal into the periapical tissue, pain and inflammation may occur.

Hitherto it has been customary to determine the apex by means of X-ray images, in practice with measuring files being introduced into the root canal. It transpired, however, that the radiological apex differs considerably from the anatomical apex: the anatomical apex is the point of the tooth that, morphologically, lies furthest from the chewing surface of the tooth; the radiological apex, however, is the point lying (geometrically) furthest from the chewing surface. As a consequence, incorrect determination of the length of the root canal occurred frequently, resulting in the problems described above. Moreover, it was often necessary to take several X-ray images per root canal, since the canal lengths can change when canal curvatures are straightened out, which necessitated considerable effort and resulted in the patient being subjected to a considerable radiation dose.

As a consequence, measurements of impedances were therefore carried out: a root canal instrument is connected to an endometry apparatus; current is supplied to the root canal via the root canal instrument, a hand or lip electrode being used as counter-electrode. When the resistance between the measuring electrode and the counter-electrode reaches a specific value, the tip of the instrument has reached the apex.

According to a further method of the prior art, gutta-percha points are coated with a conductive layer, for example, by dipping or vapor deposition, then inserted into the root canal and the impedance is measured. Gutta-percha points treated in that manner cannot, however, be joined to one another even by heating. Moreover, the silver used for the coating becomes corroded, which may result in problems given the large surface of the coating.

The goal of the present invention is accordingly to provide a root canal filling means that overcomes the mentioned disadvantages of the prior art. In particular, the position of the filling material in a root canal is to be able to be determined precisely, the material is then ideally to be able to remain in the canal and the canal is to be able to be filled in the customary manner.

SUMMARY OF THE INVENTION

Those problems are solved according to the invention by the provision of a filling means (1) for root canals in humans and animals, having a proximal end (5) and a distal end (4), which filling means includes an elongate electrically conductive element (2) sheathed in an isoprene-based matrix (3), wherein that the distal end (4) of the electrically conductive element lies exposed.

DETAILED DESCRIPTION OF THE PREFERRED EMBODIMENT

Figure 1:
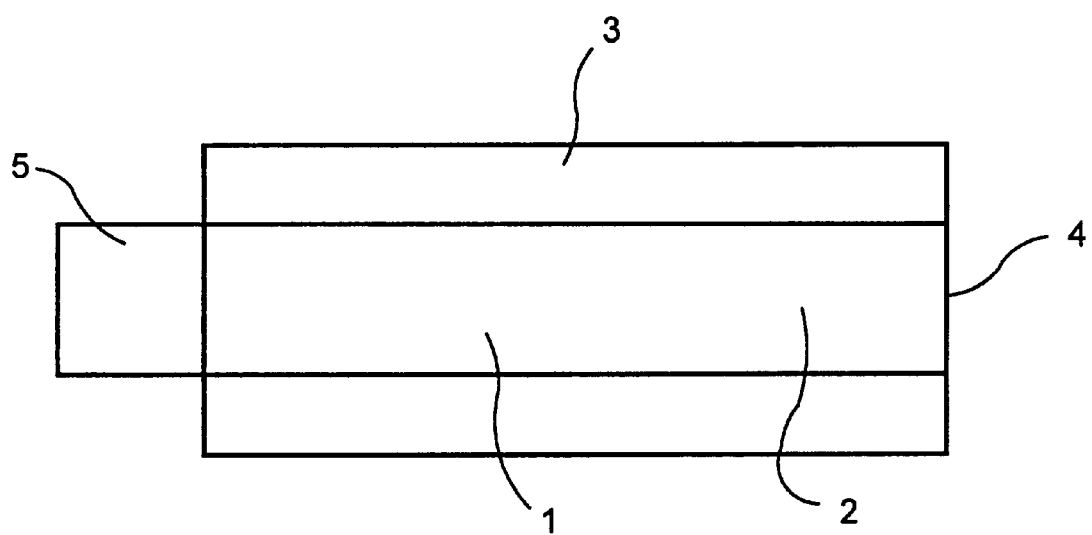
FIG. 1 shows a preferred embodiment of the present invention.

The filling has the advantage that its position in the root canal can be determined precisely by measuring the impedance or the resistance of a current flowing through the electrically conductive element and the jaw, and the means can remain in the canal. Moreover, it can be joined to other customary means, such as, for example, gutta-percha points, by heating, condensation, or by the introduction of a sealer.

The term "elongate" is preferably so defined that the extent of the means or of the element in one of the three dimensions is at least twice as large as in each of the other two dimensions individually.

Preferably the filling means according to the invention includes a distal end (4) of the electrically conductive element which remains exposed for measuring impedance or resistance. The distal end face of the filling means according to an especially preferred embodiment is formed by a cut plane (4) that extends approximately perpendicular to the longitudinal axis of the electrically conductive element and the electrically conductive element terminating in the cut plane.

According to a preferred embodiment, the proximal end (5) of the filling means (1) is free of the isoprene-based sheathing (3), with the result that a customary device for measuring impedance or resistance can be connected at that site. After the final positioning of the means in the root canal, the proximally projecting portion of the electrically conductive element can be removed and a certain amount of an isoprene-based material can be applied to cover the means.

In the attached FIGURE, which shows a preferred embodiment of the present invention, (1) denotes the filling means according to the invention, (2) denotes the elongate electrically conductive element, (3) is the isoprene-based matrix, (4) is the exposed distal end and (5) is the proximal end of the electrically conductive element without sheathing.

Preferably the isoprene-based matrix comprises trans-polyisoprene, gutta-percha, balata or a mixture thereof, with gutta-percha being preferred. In the description of the present invention, the term "gutta-percha" is to comprise also isoprene, trans-polyisoprene or balata. Preferably, however, it denotes only gutta-percha itself. The gutta-percha is preferably colorless trans-polyisoprene. According to the invention the matrix comprises at least 80% by weight of trans-polyisoprene.

Especially preferably the means according to the invention is in the form of a customary gutta-percha point.

The means according to the invention may additionally comprise additives, such as fillers, X-ray contrast agents, pharmaceutical active ingredients, such as an antibacterially active composition which is an antibiotic or glucocosticoid surfactants, waxes and resins.

As fillers there may be used, for example, substances customary per se, such as zinc oxide, silicon dioxide, aluminum oxide, calcium hydroxide or mixtures thereof in amounts customary per se.

A filling means according to the invention may preferably comprise a titanium wire having a diameter of 0.1 mm sheathed in a matrix that comprises.

(a) from 1 to 99% by weight of gutta-percha,
(b) from 1 to 99% by weight of filler,
(c) optionally additionally up to 50% by weight of X-ray contrast agent, based on (a) and (b), and
(d) optionally additional customary components.

For example, the matrix may comprise:

(a) approximately 43.5% by weight of gutta-percha,
(b) approximately 56.5% by weight of zinc oxide as sole inorganic filler,
(c) optionally additionally up to 50% by weight of X-ray contrast agent, based on (a) and (b), and
(d) optionally additional customary components.

The means according to the invention thus has basically four components, which will be explained thereinafter in greater detail.

Component 1

The (external) mechanical properties of a filling means according to the invention are determined primarily by the properties of the matrix which constitutes, for example, from 43.5 to 65.0% by weight together with from 35.0 to 56.5% by weight of filler (component 2). The matrix must, on the one hand, be elastic so that it can be processed readily and introduced easily into the root canal. It must, on the other hand, have plastic properties so that the root canal can be filled permanently without a gap remaining at the wall. Moreover, the matrix must be able to take up other components readily, especially the filler, and must adhere firmly to the electrically conductive element. For those purposes, a matrix comprising at least 80% by weight of trans-polyisoprene has proved advantageous. Gutta-percha may be mentioned by way of example, which is a naturally based matrix, the main component of which is transpolyisoprene. Other trans-polyisoprenes may of course also be used, such as balata, synthetic isoprene-based matrices or derivatives of the mentioned materials.

Component 2

The filling means according to the invention may comprise calcium hydroxide, zinc oxide, aluminum oxide, silicon dioxide or the like as filler. That filler is present, for example, in an amount of from 35.0 to 56.5% by weight together with from 43.5 to 65.0% by weight of matrix.

Zinc oxide may be present in an amount of at least 60% by weight, preferably at least 70% by weight, based on the total composition (not including the point).

The filling means can be rolled in powder form into gutta-percha, which greatly simplifies the preparation process.

Calcium hydroxide can buffer the increase of pH that usually occurs in inflammatory processes. It may therefore be desirable to introduce as much calcium hydroxide into the root canal as possible. The proportion of calcium hydroxide in the filling means according to the invention will therefore be based, on the one hand, upon that criterion and, on the other hand, upon the capacity of the matrix to take up the filler. An example of a filing means having a very high proportion of filler is a gutta-percha sheathing comprising approximately 56.5% by weight of calcium hydroxide together with approximately 43.5% by weight of gutta-percha.

Component 3

A further optional (although customary) component that may be provided is an X-ray contrast agent. X-ray contrast agents may be selected, for example, from the group consisting of zinc, ytterbiuim, yttrium, gadolinium, zirconium, strontium, tungsten, tantalum, niobium, barium, bismuth, molybdenum and lanthanum powders, powdered alloys thereof, oxides, fluorides, sulphates, carbonates, tungstates and carbides thereof, and mixtures thereof. The position of the means can thus additionally be monitored and documented by means of an X-ray image.

That component may be provided in an amount of up to 50% by weight based on matrix and filler.

Component 4

The means according to the invention comprises an elongate electrically conductive element sheathed in a matrix. The element will preferably be up to 7 cm, preferably up to 5 cm, in length, and will have a diameter of approximately 0.1 mm.

In an especially preferred embodiment, the elongate electrically conductive element is a biocompatible stable element that is resistant in the tooth, such as titanium. Preferably there is used titanium wire having a diameter of up to 1 mm, preferably up to 0.5 mm, especially of approximately 0.2 mm and more especially of approximately 0.1 mm. The wire may be of any desired cross-section, such a rotationally symmetrical, cylindrical or elliptical.

A goal of the present invention is also to provide a method of preparing such a means.

According to a further embodiment of the invention, a method of preparing a filing a means according to the invention is accordingly provided, it includes (a) a film of an isoprene-based matrix is formed,
(b) there are rolled into the matrix film optionally a filler, an X-ray contrast agent and further optional customary auxiliaries, and
(c) an electrically conductive element is sheathed with the film.

According to a preferred embodiment, the film is comminuted and extruded before step (c).

The invention will be explained hereinafter in greater detail by means of an Example. The following Example is intended to illustrate, but not limit, the invention:

EXAMPLE

To prepare a gutta-percha sheathing, gutta-percha was first rolled between a carrier roller and a pressure roller, with the result that the gutta-percha lay around the carrier roller in the form of a thin film or like a skin. Powdered zinc oxide in a weight ratio of 56.5% zinc oxide: 43.5% gutta-percha was then rolled into a film that had been produced, the film was peeled away from the carrier roller and the peeled-away film was comminuted and extruded to a thin wire-like strand. That strand is then cut up and rolled again, and then rolled around a titanium wire having a diameter of 0.1 mm in such a manner that at one (proximal) side a free portion of approximately 1 cm of the titanium wire projected from the sheathing. At a distance of approximately 5 cm from the tip of the exposed titanium wire, at the other (distal) side the titanium wire and the sheathing were severed smoothly.

It was then possible for the resulting filling means to be readily inserted into a root canal and for the depth of the root canal to be determined easily by impedance measurement and correspondingly optimized. After the insertion of the filling means, it was possible to introduce further gutta-percha points into the root canal by lateral condensation and to seal the canal without gaps.

What is claimed is:

1. A fling means (1) for root canals in humans and animals, having a proximal end (5) and a distal end (4) for inserting into the apex of the root canal, wherein said filling means comprises an electrically conductive wire (2) sheathed in an isoprene-based matrix (3), and wherein the distal end (4) of the electrically conductive wire is not covered by the isoprene-based matrix and the wire lies exposed.

2. The filling means according to claim 1, wherein the distal end of the filling means is formed by a cut plane extending approximately perpendicular to the longitudinal axis of the electrically conductive wire, the electrically conductive wire terminating in the cut plane.

3. The filing means according to claim 1, wherein the proximal end of the filling means is free of the sheathing.

4. The filling means according to claim 1, wherein the electrically conductive is titanium wire.

5. The filling means according to claim 1, wherein the matrix comprises a compound selected from the group consisting of trans-polyisoprene, gutta-percha balata, and mixtures thereof.

6. The filling means according to claim 1, wherein the matrix comprises at least 80% by weight trans-polyisoprene.

7. The filling means according to claim 1, wherein the matrix further comprises one or more additives selected from the group consisting of fillers, X-ray contrast agents, pharmaceutically active ingredients, waxes, resins, and mixtures thereof.

8. The filling means according to claim 7, wherein the matrix comprises a filler selected from the group consisting of calcium hydroxide, zinc oxide, silicon dioxide, aluminum oxide, and mixtures thereof.

9. The filling means according to claim 7, wherein the matrix comprises a pharmaceutically active ingredient that is either soluble or dispersible in an aqueous media.

10. The filling means according to claim 9 wherein the pharmaceutically active ingredient is an antibacterially active composition.

11. The filling means according to claim 10, wherein the antibacterially active composition is an antibiotic and/or a glucocorticoid.

12. The filling means according to claim 7, wherein the matrix comprises an X-ray contrast agent selected from the group consisting of zinc, ytterbium, yttrium, gadolinium, zirconium, strontium, tungsten, tantalum, niobium, barium, bismuth, molybdenum powders, lanthanum powders, powdered alloys thereof, oxides, fluorides, sulphates, carbonates, tungstates, carbides, and mixtures thereof.

13. A method of preparing a filling means for root canals in humans and animals comprising the following steps:
    (a) forming a film of an isoprene matrix,
    (b) optionally rolling into the film one or more additives selected from the group consisting of fillers, X-ray contrast agents pharmaceutically active ingredients, waxes, resins, and mixtures thereof,
    (c) sheathing an electrically conductive wire with the film, and
    (d) smoothly severing the electrically conductive wire and the sheathing, whereby exposing the wire.

14. The method according to claim 13, wherein the film is comminuted and extruded before step (c).

* * * * *